United States Patent [19]

Lee et al.

[11] Patent Number: 5,239,082

[45] Date of Patent: Aug. 24, 1993

[54] SULFONAMIDE TETRAZOLE ACAT INHIBITORS

[75] Inventors: Helen T. Lee, Ann Arbor; Drago R. Sliskovic, Ypsilanti, both of Mich.

[73] Assignee: Warner-Lambert Company, Morris Plains, N.J.

[21] Appl. No.: 924,113

[22] Filed: Aug. 3, 1992

[51] Int. Cl.$^5$ .......................................... C07D 257/02
[52] U.S. Cl. ..................................... 548/252; 548/253
[58] Field of Search ................. 548/252, 253; 514/381

[56] References Cited

U.S. PATENT DOCUMENTS

| | | | |
|---|---|---|---|
| 4,401,817 | 8/1983 | Paget et al. | 548/252 |
| 4,505,919 | 3/1985 | Cooper et al. | 548/252 |
| 4,675,335 | 6/1987 | Baker et al. | 548/252 |
| 4,711,903 | 12/1987 | Mueller et al. | 548/252 |
| 4,999,345 | 3/1991 | Schmied et al. | 548/252 |
| 5,140,038 | 8/1992 | Witte et al. | 548/252 |

Primary Examiner—David B. Springer
Attorney, Agent, or Firm—Ronald A. Daignault

[57] ABSTRACT

Pharmaceutically useful compounds having ACAT inhibitory activity of the formula

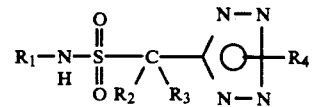

wherein $R_1$ is phenyl, substituted phenyl, naphthyl, substituted naphthyl, a heteroaromatic group or a hydrocarbon group having from 1 to 18 carbon atoms; $R_2$ and $R_3$ are hydrogen, fluoro, alkyl, alkenyl, cycloalkyl, phenyl, substituted phenyl, a heteroaryl, or form a spiroalkyl group, and $R_4$ is a hydrocarbon group having from 1 to 20 carbon atoms.

18 Claims, No Drawings

SULFONAMIDE TETRAZOLE ACAT INHIBITORS

The present invention describes a series of novel sulfonamide tetrazoles which inhibit acyl-CoA: cholesterol acyltransferase (ACAT), the enzyme responsible for the esterification of dietary cholesterol. Such agents may decrease the absorption of dietary cholesterol and therefore provide a therapy for individuals with hypercholesterolemia.

SUMMARY OF THE INVENTION

The compounds of the present invention can be described by the following general formula

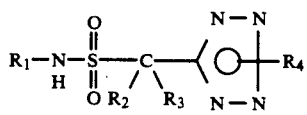

Formula I wherein $R_1$ is selected from
  (a) phenyl which is unsubstituted or is substituted with from one to three substituents selected from: alkyl having from 1 to 4 carbon atoms and which is straight or branched, alkoxy having from 1 to 3 carbon atoms and which is straight or branched, alkythio having from 1 to 3 carbon atoms and which is straight or branched, hydroxy, fluorine, chlorine, bromine, phenyl, nitro, cyano, trifluoromethyl, —COOH, —COOalkyl wherein alkyl has from 1 to 4 carbon atoms and which is straight or branched, —(CH$_2$)$_m$NR$_5$R$_6$ wherein m is zero or one, and each of R$_5$ and R$_6$ is hydrogen or a straight or branched alkyl group having 1 to 4 carbon atoms;
  (b) 1- or 2-naphthyl which is unsubstituted or substituted with one to three substituents selected from: alkyl having from 1 to 4 carbon atoms and which is straight or branched, alkoxy having from 1 to 3 carbon atoms and which is straight or branched, hydroxy, fluorine, chlorine, bromine, nitro, cyano, trifluoromethyl, —COOH, —COOalkyl wherein alkyl has from 1 to 4 carbon atoms and is straight or branched, —(CH$_2$)$_m$NR$_5$R$_6$ wherein m, R$_5$, and R$_6$ have the meanings defined above;
  (c) the group

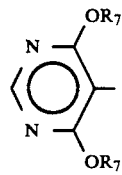

wherein R$_7$ is a lower alkyl group having from 1 to 3 carbon atoms and is straight or branched;
  (d) the group

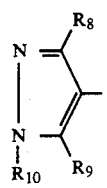

wherein R$_8$ and R$_9$ are straight or branched alkyl having from 1 to 4 carbon atoms or phenyl, and R$_{10}$ is a straight or branched hydrocarbon group having from 1 to 18 carbon atoms which is saturated or is unsaturated containing one double bond or two nonadjacent double bonds; phenyl; phenyl substituted with from one to three substituents selected from straight or branched alkyl having 1 to 4 carbon atoms, straight or branched alkoxy having from 1 to 3 carbon atoms, hydroxy, fluorine, chlorine, bromine, nitro, cyano, trifluoromethyl, —COOH, —COOalkyl wherein alkyl has from 1 to 4 carbon atoms and is straight or branched or (CH$_2$)$_m$NR$_5$R$_6$ wherein m, R$_5$, and R$_6$ are as defined above; or a heterocyclic group selected from 2-, 3-, or 4-pyridyl, 2-, 4-, or 5-pyrimidinyl, 2- or 3-pyrazinyl, 2-, 3-, 4-, 5-, 6-, 7-, or 8-quinolinyl, or 3- or 4-pyridazinyl and the N oxides thereof;
  (e) the group

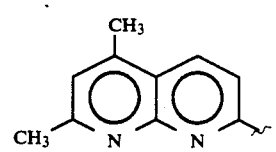

(f) the group

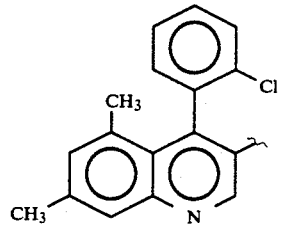

(g) a straight or branched hydrocarbon group having from 1 to 18 carbon atoms which is saturated or is unsaturated containing one double bond or two nonadjacent double bonds;
  (h) a cycloalkyl group having from 3 to 8 carbon atoms, or
  (i) a heteroaromatic group selected from 2-, 3-, or 4-pyridyl which is unsubstituted or substituted with an alkyl group having from 1 to 4 carbon atoms or 2-, 4-, or 5-pyrimidinyl, and the N-oxides thereof;
  (j) the group

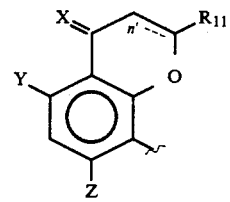

wherein—denotes a single or double bond; Y and Z are each independently hydrogen, a straight or branched alkyl group of 1 to 4 carbon atoms, an alkoxy group of 1 to 3 carbon atoms, or halo; X is oxygen or two hydrogen atoms; R$_{11}$ is hydrogen or a straight or branched alkyl group of 1 to 4 carbon atoms, and n' is zero or one; or (k) is selected from the group

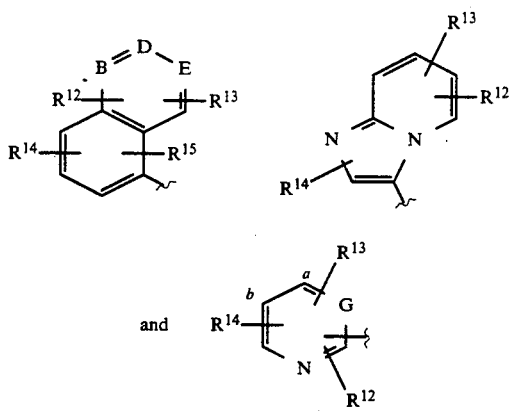

wherein $R^{12}$, $R^{13}$, $R^{14}$, and $R^{15}$ are each independently hydrogen, halo, a straight or branched alkyl group of 1 to 4 carbon atoms, an alkoxy group of 1 to 3 carbon atoms, an alkylthio group of 1 to 3 carbon atoms, cycloalkylthio of 5 to 7 carbon atoms, phenylalkylthio in which alkyl is 1 to 4 carbon atoms, substituted phenylthio, heteroarylthio, or heteroaryloxy; and B, D, E, and G are nitrogen or carbon where one or more of B, D, and E is nitrogen; with the proviso that when $G=N$ the group is attached to the nitrogen atom of Formula I at the 4 or 5 position of the pyrimidine ring (a and b), wherein $R_2$ and $R_3$ are the same or different and are selected from:

(a) hydrogen or fluoro;
(b) a straight or branched alkyl group having from 1 to 12 carbon atoms;
(c) a phenyl or phenylalkyl group where alkyl is from 1 to 4 carbon atoms and which phenyl is unsubstituted or substituted with from 1 to 3 substituents selected from straight or branched alkyl having from 1 to 4 carbon atoms, straight or branched alkoxy having from 1 to 4 carbon atoms alkythio (straight or branched), hydroxy, fluorine, chlorine, bromine, trifluoromethyl, cyano, nitro, phenyl, or $(CH_2)_mNR_5R_6$ wherein m, $R_5$, and $R_6$ have the meanings defined above;
(d) a straight or branched alkenyl group having from 2 to 6 carbon atoms;
(e) a cycloalkyl group having from 3 to 8 carbon atoms; or
(f) $R_2$ and $R_3$ taken together with the carbon atom to which they are attached form a spiroalkyl group having from 3 to 7 carbon atoms; or
(g) when $R_2$ is hydrogen, F, alkyl of $C_{1-12}$ atoms, $R_3$ is a heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with an alkyl group having from 1 to 4 carbon atoms and the N oxides thereof;
(h) $R_2$ and $R_3$ taken together with the carbon atom to which they are attached form an alkylidene group of 1 to 4 carbon atoms, a benzylidene group;
(i) 1- or 2-naphthyl which is unsubstituted or substituted with one to three substituents selected from: alkyl having from 1 to 4 carbon atoms and which is straight or branched, alkoxy having from 1 to 3 carbon atoms and which is straight or branched; wherein $R_4$ is a straight or branched hydrocarbon chain having from 1 to 20 carbon atoms and is saturated or is unsaturated and has 1 double bond or has 2 nonadjacent double bonds; pharmaceutically acceptable salts and individual enantiomeric isomers of the compounds.

Pharmaceutically acceptable salts of the compounds of Formula I are also included as a part of the present invention. Suitable acids for forming acid salts of the compounds of Formula I containing a basic group include, but are not necessarily limited to acetic, benzoic, benzenesulfonic, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

Illustrative examples of straight or branched saturated hydrocarbon chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undeoyl, n-dodecyl, n-hexadecyl, 2,2-dimethyldodecyl, 2-tetradecyl, and n-octadecyl groups.

Illustrative examples of straight or branched hydrocarbon chains having from 1 to 20 carbon atoms and having 1 double bond or 2 nonadjacent double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having 1 to 3 carbon atoms include methoxy, ethoxy, n-propoxy, and isopropoxy.

Straight or branched alkyl groups having from 1 to 4 carbon atoms include, for example, methyl, ethyl, n-propyl, isopropyl, and n-butyl.

Cycloalkyl groups having from 3 to 8 carbon atoms which $R_1$ may represent are cyclopropyl, cyclobutyl, cyclopentyl, cyclohexyl, cycloheptyl, and cyclooctyl. Preferred groups have 5 to 8 carbon atoms.

A 5- or 6-membered monocyclic or fused bicyclic heterocycle is a monocyclic or fused bicyclic aromatic ring containing at least one to four heteroatoms in at least one ring, such as nitrogen, oxygen, or sulfur or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocyclic containing a nitrogen atom.

More specifically, such a heterocycle may be a 2- or 3-thienyl; 2-, or 3-furanyl; 2-, or 3-, or 4-pyridyl or 2-, or 3-, or 4-pyridinyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5-tetrazolyl; 3- or 5-(1,2,4)-triazolyl; 4- or 5-(1,2,3)-triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Preferred compounds of the present invention are those of Formula I wherein $R_1$ is substituted phenyl; $R_2$ and $R_3$ are each independently hydrogen, fluoro, alkyl from 1 to 12 carbon atoms, cycloalkyl having from 5 to 8 carbon atoms, phenyl, benzyl, or naphthyl, and $R_4$ has 8 to 18 carbon atoms. Also preferred compounds of this invention are those wherein the $R_4$ substituent group is attached to the 2-position.

More preferred compounds of the present invention are those of Formula I wherein $R_1$ is 2,6-bis (1-methylethyl)phenyl or 2,4,6-trimethoxyphenyl; $R_2$ and $R_3$ are each independently hydrogen, fluoro, alkyl from 1 to 12 carbon atoms, cyclohexyl, phenyl, benzyl, or naphthyl, and $R_4$ has 8 to 18 carbon atoms.

Particularly valuable are the following:

N-[2,6-bis(1-methylethyl)phenyl]-2-dodecyl-α-methyl-α-phenyl-2H-tetrazole-5-methanesulfonamide, N-[2,6-bis(1-methylethyl)phenyl]-2-dodecyl-α-cyclohexyl-2H-tetrazole-5-methanesulfonamide, N-[2,6-bis(1-methylethyl)phenyl]-2-dodecyl-α-benzyl-2H-tetrazole-5-methanesulfonamide, N-[2,6-bis(1-methylethyl)phenyl]-2-dodecyl-α-phenyl-2H-tetrazole-5-methanesulfonamide, 2-Dodecyl-α-methyl-α-phenyl-N-(2,4,6-trimethoxyphenyl)-2H-tetrazole-5-methanesulfonamide, N-(2,4,6-trimethoxyphenyl)-2-dodecyl-α-cyclohexyl-2H tetrazole-5-methanesulfonamide, N-(2,4,6-trimethoxyphenYl)-2-dodecyl-α-benzyl-2H-tetrazole-5-methanesulfonamide, N-(2,4,6-trimethoxyphenyl)-2-dodecyl-α-phenyl-2H-tetrazole-5-methanesulfonamide, N-[2,6-bis(1-methylethyl)phenyl]-2-dodecyl-α-(1-naphthyl)-2H-tetrazole-5-methanesulfonamide, N-[2,6-bis(1-methylethyl)phenyl]-2-dodecyl-α-cyclohexyl-α-methyl 2H-tetrazole-5-methanesulfonamide, N-[2,6-bis(1-methylethyl)phenyl]-2-dodecyl-α-dodecyl-2H-tetrazole-5-methanesulfonamide, N-[2,6-bis(1-methylethyl)phenyl]-2-dodecyl-α-fluoro-α-phenyl-2H-tetrazole-5-methanesulfonamide, N-(2,4,6-trimethoxyphenyl)-2-dodecyl-α-(1-naphthyl)-2H-tetrazole-5-methanesulfonamide, N-(2,4,6-trimethoxyphenyl)-2-dodecyl-α-cyclohexyl-α-methyl-2H-tetrazole-5-methanesulfonamide, N-(2,4,6-trimethoxyphenyl)-2-dodecyl-α-dodecyl-2H-tetrazole-5-methanesulfonamide, and N-(2,4,6-trimethoxyphenyl)-2-dodecyl-α-fluoro-α-phenyl-2H-tetrazole-5-methanesulfonamide.

As shown by the data presented below in Table 1, the compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field FJ, Salone RG. Biochemica et Biophysica 1982;712:557-70. The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as $IC_{50}$ values; i.e., the concentration of test compound required to inhibit the activity of the enzyme by 50%.

TABLE 1

| Example | Name | IAI $IC_{50}$ (μM) | APCC (% ΔTC) (30 mg/kg) |
|---|---|---|---|
| 1 | N-[2,6-bis(1-methylethyl)phenyl]-2-dodecyl-2H-tetrazole-5-methanesulfonamide | 0.222 | −61 |
| 2 | N-[2,6-bis(1-methylethyl)phenyl]-2-hexadecyl-2H-tetrazole-5-methanesulfonamide | 0.60 | −20 |
| 3 | N-[2,6-bis(1-methylethyl)phenyl]-2-tetradecyl-2H-tetrazole-5-methanesulfonamide | 0.15 | −42 |
| 4 | N-[2,6-bis(1-methylethyl)phenyl]-2-octyl-2H-tetrazole-5-methanesulfonamide | 0.75 | −14 |
| 5 | N-[2,6-bis(1-methylethyl)]-2-octadecyl-2H-tetrazole-5-methanesulfonamide | 7.6 | −31 |
| 6 | N-[2,6-bis(1-methylethyl)phenyl]-1-dodecyl-1H-tetrazole-5-methanesulfonamide | 1.2 | −41 |
| 7 | N-(2,4,6-trimethoxyphenyl)-2-dodecyl-2H-tetrazole-5-methanesulfonamide | 0.18 | −60 |
| 8 | N-(2,4,6-trimethoxyphenyl)-1-dodecyl-1H-tetrazole-5-methanesulfonamide | 3.7 | −30 |
| 9 | N-[2,6-bis(1-methylethyl)phenyl]-2-dodecyl-α, α-dimethyl-2H-tetrazole-5-methanesulfonamide | 0.04 | −53 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention also appear in Table 1.

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of the present invention can be prepared by various routes all of which are generally known in the art.

In Chart I, sulfoacetic acid 1 in refluxing ethanol gives 2. Reaction of 2 with POCl$_3$ at 125° C. gives 3. 3 is then treated with an aniline (trisubstituted or disubstituted) in the presence of Et$_3$N in an inert solvent (THF or ether) to give 4. Compound 4 was hydrolyzed using KOH in aqueous ethanol and then reacted with (COCl)$_2$ in toluene to give 5. Gaseous ammonia was passed through 5 in toluene to give 6. The amide 6 was treated with tosyl chloride in pyridine to give 7. Compound 7 was reacted under reflux in dioxane with Bu$_3$SnN$_3$ to give 8. 8 was reacted with different alkyl halides in refluxing CH$_3$CN in the presence of Et$_3$N to give predominately regioisomer 9 and a trace amount of 10, which were readily separated by silica gel chromatography.

Sodium hydride was added to a solution of 9 in THF, followed by chloromethyl methyl ether. The protected 11 was then treated with NaH and an alkyl halide to give a monoalkylated analog of Compound 11. Similarly, a second equivalent of base may then be added, followed by an appropriate alkyl halide to give disubstituted analogs of Compound 11. Finally, the protecting group was removed by BBr$_3$ to give 13.

EXAMPLE 1

N-2,6-Bis(1-methylethyl)phenyl]-2-dodecyl-2H-tetrazole-5-methanesulfonamide (a) Ethyl [[[2,6-bis(1-methylethyl)phenyl]amino]sulfonyl]acetate Sulfoacetic acid (52 g, 371 mM) and EtOH (500 mL) were heated under reflux for 20 hours. The reaction mixture was cooled, and the excess ethanol was removed under vacuum to give 2 (see Chart I). A mixture of 2 (16.82 g, 100 mM) and POCl$_3$ (30.67 g, 200 mM) was heated at 125° C. for 5 hours. The mixture was cooled and filtered, and excess POCl$_3$ was removed to give 3 (see Chart I). Compound 3 (8.18 g, 43.83 mM) was added dropwise with stirring to a solution of 2,6-diisopropylaniline (15.54 g, 87.66 mM) in 50 mL CH$_2$Cl$_2$ maintained at 0° C. The mixture was stirred at room temperature for an additional 18 hours. The solvent was removed and the residue was redissolved in 100 mL ethyl acetate and washed with 1 N HCl and brine. The ethyl acetate was evaporated and the pure compound was isolated by chromatography over silica gel (EtOAc/hexane, 1:4 as eluant) as a white powder, 7.0 g (~50%), mp 114°-116° C.

(b) [[[2,6-Bis(1-methylethyl)phenyl]amino]sulfonyl]acetyl chloride

Ethyl [[[2,6-bis(1-methylethyl)phenyl]amino]sulfonyl]acetate (4.9 g, 15 mM) and KOH (2.1 g, 37.5 mM) were mixed in 15 mL H$_2$O and 6 mL EtOH. The mixture was heated under reflux for 2.5 hours, charcoal was added, and heating was continued for another 10 minutes. The mixture was filtered while hot and then extracted with ether, the aqueous portion was acidified with concentrated HCl, and extracted with 2×100 mL portions of ether. The ether extracts were combined and evaporated to yield a total weight of 1.49 g (33%) of the corresponding acid. The acid was suspended in 20 mL toluene, and 1 mL (COCl)$_2$ (excess) was added, followed by two drops of DMF. The mixture was stirred at room temperature overnight. The excess (COCl)$_2$ and solvent was removed to yield 1.57 g (~100%) of crude acid chloride. NMR (CDCl$_3$) δ 1.3 (d, 12H), 3.22-3.5 (m, 2H), 4.05 (s, 2H), 6.5 (s, 1H), 7.2-7.4 (m, 3H) ppm.

(c) N-[2,6-Bis(1-methylethyl)phenyl]-2H-tetrazole-5-methanesulfonamide

Gaseous NH$_3$ was passed into a solution of material from step (b) above (1.57 g, 4.9 mM) in 50 mL dry toluene, and the mixture was stirred at room temperature for 18 hours. The product, N-[[[2,6-bis(1-methylethyl)phenyl]amino]sulfonyl]acetamide, was collected by filtration. Tosyl chloride (0.953 g, 5 mM) was added slowly to a solution of the above sulfonamide (1.5 g, 5 mM) in 1 mL pyridine, the dark solution was stirred at room temperature for an additional hour. Water (10 mL) and EtOAc (10 mL) was added, and organic layer was washed with 1 N HCl and water, dried, and evaporated to dryness. The pure N-[2,6-bis(1-methylethyl)-phenyl]cyanomethanesulfonamide (0.75 g, 53%) was isolated by chromatography (1:1 hexane:EtOAc a solvent). A mixture of the above nitrite (0.750 g, 2.67 mM), dioxane (10 mL), and tri-n-butyltin azide (0.900 g, 2.7 mM) were heated under reflux for 20 hours. The solvent was removed and residue dissolved in 20 mL ether, gaseous HCl was passed through the solution for 10 minutes, and the solvent was evaporated to dryness. The product named above was washed with hexane and collected by filtration (total weight 0.5 g (57%), mp 195°-197° C.).

(d)
N-[2,6-Bis(1-methylethyl)phenyl]-2-dodecyl-2H-tetrazole-5-methanesulfonamide Dodecyl bromide (0.386 g, 1.55 mM) was added dropwise to a solution of N-[2,6-bis(1-methylethyl) phenyl]-2H-tetrazole-5-methanesulfonamide (0.5 g, 1.55 mM), Et$_3$N (0.157 g, 1.55 mM) in CH$_3$CN (50 mL), and heated for 20 hours. The residue from solvent removal was redissolved in 20 mL EtOAc, washed with 0.1 N HCl, brine, and evaporated. N-[2,6-Bis(1-methylethyl) phenyl]-2-dodecyl-2H-tetrazole-5-methanesulfonamide was isolated by chromatography (0.13 g, 22%), mp 85°-86° C., along with trace amounts of N-[2,6-bis(1-methylethyl)phenyl]-1-dodecyl-1H-tetrazole-5-methanesulfonamide.

The following compounds were prepared according to Example 1.

| Example | Name | Melting Point |
| --- | --- | --- |
| 2 | N-[2,6-bis(1-methylethyl) phenyl]-2-hexadecyl-2H-tetrazole-5-methane-sulfonamide | 55-57° C. |
| 3 | N-[2,6-bis(1-methylethyl) phenyl]-2-tetradecyl-2H-tetrazole-5-methane-sulfonamide | 64-66° C. |
| 4 | N-[2,6-bis(1-methylethyl) phenyl]-2-octyl-2H-tetrazole-5-methane-sulfonamide | 89-94° C. |
| 5 | N-[2,6-bis(1-methylethyl) phenyl]-2-octadecyl-2H-tetrazole-5-methane-sulfonamide | 53-55° C. |
| 6 | N-[2,6-bis(1-methylethyl) phenyl]-1-dodecyl-1H-tetrazole-5-methane-sulfonamide | 70-72° C. |
| 7 | N-(2,4,6-trimethoxy phenyl)-2-dodecyl-2H-tetrazole-5-methane-sulfonamide | 55-57° C. |
| 8 | N-(2,4,6-trimethoxy phenyl),-1-dodecyl-1H-tetrazole-5-methane-sulfonamide | 102-104° C. |

EXAMPLE 9

N-[2,6-Bis(1-methylethyl)phenyl]-2-dodecyl-α,α-dimethyl-2H-tetrazole-5-methanesulfonamide Sodium hydride (0.22 g, 5.5 mM), was added to a solution of N-[2,6-bis(1-methylethyl)phenyl]-2-dodecyl-2H-tetrazole-5-methanesulfonamide (2.45 g, 5 mM) in dry THF (2 mL), followed by chloromethyl methyl ether (0.45 g, 5 mM). The solution was stirred at room temperature for 18 hours. EtOAc (10 mL) was added, and the reaction mixture was washed with dilute HCl, brine, dried, filtered, and evaporated. After purification by column chromatography, 2.1 g of pure N-[2,6-bis(1-methylethyl)phenyl]-2-dodecyl-N-(methoxymethyl)-2H-tetrazole-5-sulfonamide was isolated (79%). Sodium hydride (0.173 g, 43 mM) was added to a solution of N-[2,6-bis(1-methylethyl) phenyl]-2-dodecyl-N-(methoxymethyl)-2H-tetrazole-5-sulfonamide in dry THF, followed by methyl iodide (0.61 g, 43 mM). This was stirred at room temperature for 30 minutes before a second equivalent of NaH (0.173 g, 43 mM) was added; followed by a second equivalent of MeI (0.61 g, 43 mM). The solution was stirred at room temperature for 18 hours. EtOAc was added and the reaction mixture was washed with 0:1 HCl, brine, dried, filtered, and evaporated to yield: N-[2,6-bis(1-methylethyl)phenyl]-2-dodecyl-N-(methoxymethyl)-α,α-dimethyl-2H tetrazole-5-methanesulfonamide. Boron tribromide (9.4 mL, 9.372 mM) was added slowly with stirring to a solution of the previous product (2.4 g, 4.26 mM) in CH$_2$Cl$_2$ (5 mL) at −78° C. After 5 hours, a solution of NaHCO$_3$ in aqueous acetone was added and the mixture was stirred at room temperature for 1 hour. The organic layer was washed with dilute 1 N HCl, brine, dried, filtered, and evaporated. After chromatography, 1.2 g of N-[2,6-Bis(1-methylethyl)phenyl]-2-dodecyl-α,α-dimethyl-2H-tetrazole-5-methanesulfonamide was isolated as a white powder (48%), mp 63°-65° C.

EXAMPLE 10

N-[2,6-Bis(1-methylethyl)phenyl]-2-dodecyl-α-phenyl-2H-tetrazole-5-methanesulfonamide

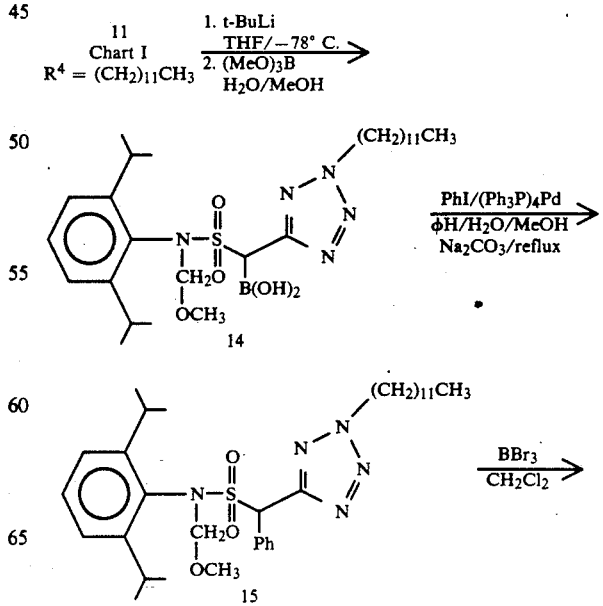

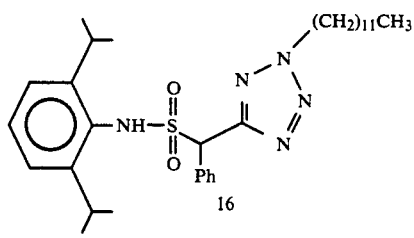

Reaction of the lithio derivative of 11 with trimethyl borate followed by hydrolysis gives the boronic acid 14. Tetrakis (triphenylphosphine) palladium (0)-catalyzed coupling of 14 with phenyl iodide gives 15. Boron tribromide removal of the MOM (methoxymethyl) protecting group in 15 gives the desired 16 (J Org Chem 1992;57:1653).

CHART I

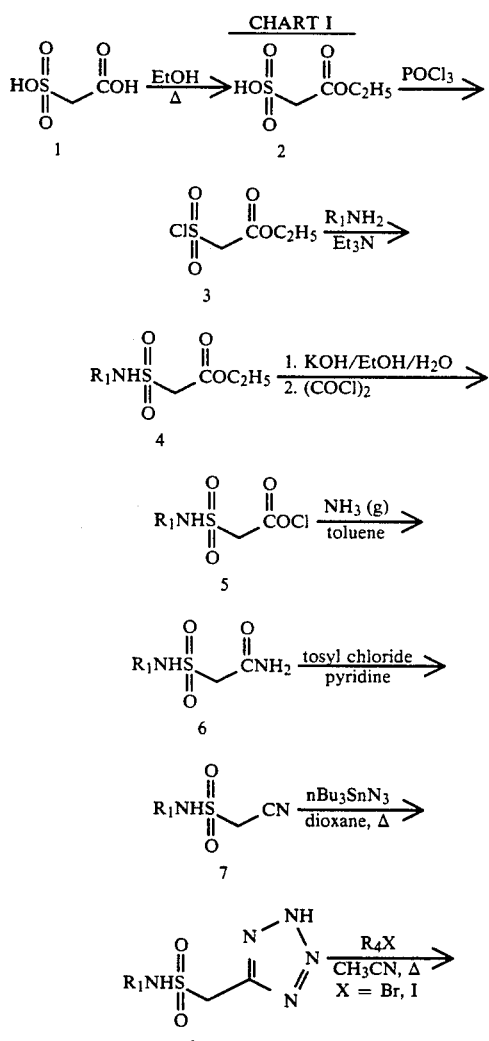

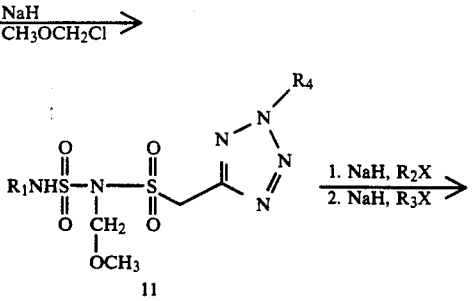

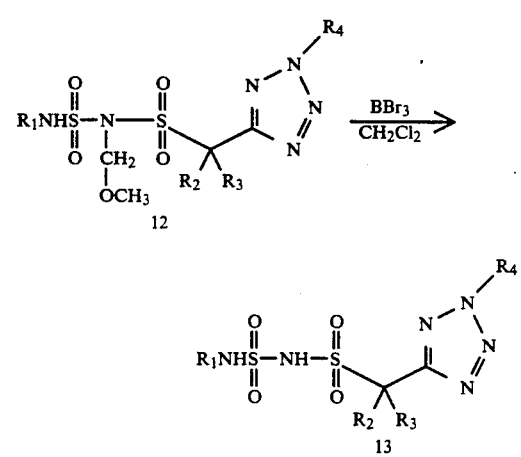

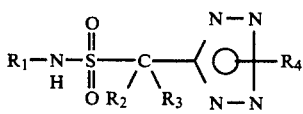

We claim:
1. A compound of the formula

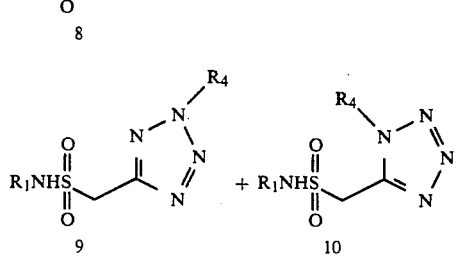

wherein $R_1$ is selected from
(a) phenyl which is unsubstituted or is substituted with from one to three substituents selected from: alkyl having from 1 to 4 carbon atoms and which is straight or branched, alkoxy having from 1 to 3 carbon atoms and which is straight or branched, alkythio having from 1 to 3 carbon atoms and which is straight or branched, hydroxy, fluorine, chlorine, bromine, phenyl, nitro, cyano, trifluoromethyl, —COOH, —COOalkyl wherein alkyl has from 1 to 4 carbon atoms and which is straight or branched, —(CH$_2$)$_m$NR$_5$R$_6$ wherein m is zero or one, and each of R$_5$ and R$_6$ is hydrogen or a straight or branched alkyl group having 1 to 4 carbon atoms and m is zero or one;
(b) 1- or 2-naphthyl which is unsubstituted or substituted with one to three substituents selected from: alkyl having from 1 to 4 carbon atoms and which is straight or branched, alkoxy having from 1 to 3 carbon atoms and which is straight or branched, hydroxy, fluorine, chlorine, bromine, nitro, cyano, trifluoromethyl, —COOH, —COOalkyl wherein alkyl has from 1 to 4 carbon atoms and is straight or branched, —(CH$_2$)$_m$NR$_5$R$_6$ wherein m, R$_5$, and R$_6$ have the meanings defined above;
(c) a straight or branched hydrocarbon group having from 1 to 18 carbon atoms which is saturated or is unsaturated containing one double bond or two nonadjacent double bonds; or (d) a cycloalkyl group having from 3 to 8 carbon atoms;

wherein each of $R_2$ and $R_3$ is the same or different and is selected from:

(a) hydrogen or fluoro;

(b) a straight or branched alkyl group having from 1 to 12 carbon atoms;

(c) a phenyl or phenylalkyl group where alkyl is from 1 to 4 carbon atoms and which phenyl is unsubstituted or substituted with from 1 to 3 substituents selected from straight or branched alkyl having from 1 to 4 carbon atoms, straight or branched alkoxy having from 1 to 4 carbon atoms, alkylthio (straight or branched), hydroxy, fluorine, chlorine, bromine, trifluoromethyl, cyano, nitro, phenyl, or $(CH_2)_m NR_5 R_6$ wherein m, $R_5$, and $R_6$ have the meanings defined above;

(d) a straight or branched alkenyl group having from 2 to 6 carbon atoms;

(e) a cycloalkyl group having from 3 to 8 carbon atoms; or (f) $R_2$ and $R_3$ taken together with the carbon atom to which they ar attached form a spiroalkyl group having from 3 to 7 carbon atoms;

(g) $R_2$ and $R_3$ taken together with the carbon atom to which they are attached form an alkylidene group of 1 to 4 carbon atoms, a benzylidene group;

(h) 1- or 2-naphthyl which is unsubstituted or substituted with one to three substituents selected from: alkyl having from 1 to 4 carbon atoms which is straight or branched, alkoxy having from 1 to 3 carbon atoms and which is straight or branched, wherein $R_4$ is a straight or branched hydrocarbon chain having from 1 to 20 carbon atoms and is saturated or is unsaturated and has 1 double bond or has 2 nonadjacent double bonds; pharmaceutically acceptable salts and individual enantiomeric isomers of the compounds.

2. A compound of claim 1 wherein $R_1$ is phenyl or substituted phenyl.

3. A compound of claim 2 wherein $R_1$ is substituted phenyl; $R_2$ and $R_3$ are each independently hydrogen, fluoro, alkyl from 1 to 12 carbon atoms, cycloalkyl having from 5 to 8 carbon atoms, phenyl, benzyl, or naphthyl, and $R_4$ has 8 to 18 carbon atoms.

4. A compound of claim 3 wherein $R_1$ is 2,6-bis (1-methylethyl)phenyl or 2,4,6-trimethoxyphenyl; $R_2$ and $R_3$ are each independently hydrogen, fluoro, alkyl from 1 to 12 carbon atoms, cyclohexyl, phenyl, benzyl or naphthyl, and $R_4$ has 8 to 18 carbon atoms.

5. A compound of claim 4 which is
N-[2,6-bis(1-methylethyl)phenyl]-2-dodecyl-α-methyl-α-phenyl-2H-tetrazole-5-methanesulfonamide,
N-[2,6-bis(1-methylethyl)phenyl]-2-dodecyl-α-cyclohexyl-2H tetrazole-5-methanesulfonamide,
N-[2,6-bis(1-methylethyl)phenyl]-2-dodecyl-α-benzyl-2H-tetrazole-5-methanesulfonamide,
2-Dodecyl-α-methyl-α-phenyl-N-(2,4,6-trimethoxyphenyl)-2H tetrazole-5-methanesulfonamide,
N-(2,4,6-trimethoxyphenyl)-2-dodecyl-α-cyclohexyl-2H tetrazole-5-methanesulfonamide,
N-(2,4,6-trimethoxyphenyl)-2-dodecyl-α-benzyl-2H-tetrazole-5-methanesulfonamide,
N-[2,6-bis(1-methylethyl)phenyl]-2-dodecyl-α-(1-naphthyl)-2H-tetrazole-5-methanesulfonamide,
N-[2,6-bis(1-methylethyl)phenyl]-2-dodecyl-α-cyclohexyl-α-methyl-2H-tetrazole-5-methanesulfonamide,
N-[2,6-bis(1-methylethyl)phenyl]-2-dodecyl-α-dodecyl-2H-tetrazole-5-methanesulfonamide,
N-[2,6-bis(1-methylethyl)phenyl]-2-dodecyl-α-fluoro-α-phenyl-2H-tetrazole-5-methanesulfonamide,
N-(2,4,6-trimethoxyphenyl)-2-dodecyl-α-(1-naphthyl)-2H-tetrazole-5-methanesulfonamide,
N-(2,4,6-trimethoxyphenyl)-2-dodecyl-α-cyclohexyl-α-methyl-2H tetrazole-5-methanesulfonamide,
N-(2,4,6-trimethoxyphenyl)-2-dodecyl-α-dodecyl-2H-tetrazole-5-methanesulfonamide, and
N-(2,4,6-trimethoxyphenyl)-2-dodecyl-α-fluoro-α-phenyl-2H-tetrazole-5-methanesulfonamide.

6. A compound of claim 4 which is N-[2,6-Bis(1-methylethyl)phenyl]-2-dodecyl-2H-tetrazole-5-methanesulfonamide.

7. A compound of claim 4 which is N-[2,6-bis(1-methylethyl)phenyl]-2-dodecyl-α-cyclohexyl-2H-tetrazole-5-methanesulfonamide.

8. A compound of claim 4 which is N-[2,6-bis(1-methylethyl)phenyl]-2-dodecyl-α-benzyl-2H-tetrazole-5-methanesulfonamide.

9. A compound of claim 4 which is N-(2,4,6-trimethoxy-phenyl)-2-dodecyl-α-methyl-α-phenyl-2H-tetrazole-5-methanesulfonamide.

10. A compound of claim 4 which is N-(2,4,6-trimethoxyphenyl)-2-dodecyl-α-cyclohexyl-2H-tetrazole-5-methanesulfonamide.

11. A compound of claim 4 which is N-(2,4,6-trimethoxyphenyl)-2-dodecyl-α-benzyl-2H-tetrazole-5-methanesulfonamide.

12. A compound of claim 4 which is N-[2,6-bis(1-methylethyl)phenyl]-2-dodecyl-α-(1-naphthyl)-2H-tetrazole-5-methanesulfonamide.

13. A compound of claim 4 which is N-[2,6-bis(1-methylethyl)phenyl]-2-dodecyl-α-cyclohexyl-α-methyl-2H-tetrazole-5-methanesulfonamide.

14. A compound of claim 4 which is N-[2,6-bis(1-methylethyl)phenyl]-2-dodecyl-α-dodecyl-2H-tetrazole-5-methanesulfonamide.

15. A compound of claim 4 which is N-[2,6-bis(1-methylethyl)phenyl]-2-dodecyl-α-phenyl-2H-tetrazole-5-methanesulfonamide.

16. A compound of claim 4 which is N-[2,6-bis(1-methylethyl)phenyl]-2-dodecyl-α,α-dimethyl-2H-tetrazole-5-methanesulfonamide.

17. A compound of claim 4 which is N-(2,4,6,-trimethoxyphenyl)-2-dodecyl-2H-tetrazole-5-methanesulfonamide.

18. A compound of claim 4 which is N-[2,6-bis(1-methylethyl)phenyl]-2-dodecyl-α-methyl-2H-tetrazole-5-methanesulfonamide.

* * * * *